United States Patent
Giannessi et al.

[11] Patent Number: 5,227,496
[45] Date of Patent: Jul. 13, 1993

[54] PYROGLUTAMIC ACID DERIVATIVES AS ENHANCERS OF LEARNING PROCESSES AND MEMORY AND PHARMACEUTICAL COMPOSITIONS COMPRISING SAME

[75] Inventors: Fabio Giannessi; Orlando Ghirardi; Roberto Cozzolino; Domenico Misiti; Maria O. Tinti, all of Rome, Italy

[73] Assignee: Sigma-Tau Industrie Farmaceutiche Riunite S.p.A., Rome, Italy

[21] Appl. No.: 864,688

[22] Filed: Apr. 7, 1992

[30] Foreign Application Priority Data

Apr. 11, 1991 [IT] Italy ............... RM91A000246

[51] Int. Cl.$^5$ ............... A61K 31/535; A61K 31/40; C07D 265/28; C07D 207/28
[52] U.S. Cl. ............... 548/519; 548/537
[58] Field of Search ............... 548/519, 537; 514/422, 514/423

[56] References Cited

U.S. PATENT DOCUMENTS

| | | | |
|---|---|---|---|
| 2,651,639 | 9/1953 | Angier | 548/537 |
| 3,051,722 | 8/1962 | Biel | 548/537 X |
| 4,933,354 | 6/1990 | Ikeguchi et al. | 514/343 |
| 5,102,882 | 4/1992 | Kimura et al. | 548/519 X |

FOREIGN PATENT DOCUMENTS

2185483 7/1987 United Kingdom ............... 548/537

OTHER PUBLICATIONS

Pharmacological Research Communications, vol. 19, No. 12, (1987) pp. 901–912 Spignoli et al.
Banfi S. and co-workers, II Farmaco—Ed. Sc.—vol. 39—fasc. 1 pp. 16–22 (1983).
Moctynuna Jul. 18, 1985 pp. 1322 through 1329 Rhim Pharm Zh. (1985).

*Primary Examiner*—Floyd D. Higel
*Attorney, Agent, or Firm*—Allegretti & Witcoff, Ltd.

[57] ABSTRACT

Orally or parenterally administrable pharmaceutical compositions in unit dosage form comprise from about 100 to about 500 mg of one of the compounds of formula (I).

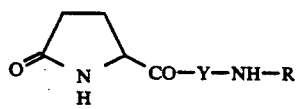

wherein R is selected from:
2-(N,N-diisopropyl)aminoethyl,
2-aminoethyl,
2-N-(pyrrolidin-2-one-1-yl)acetyl aminoethyl,
2-phenylethyl,
benzyl,
2-N-(pyroglutamylglycyl)aminoethyl,
2-N-(pyroglutamyl)aminoethyl;

Y is either a C—N single bond or the bivalent residue of an aminoacid selected from:

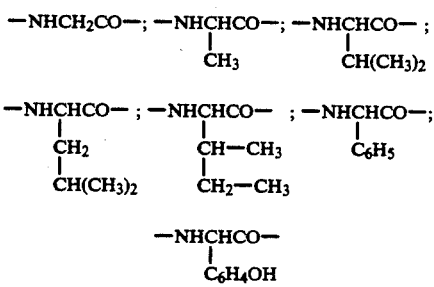

are potent enhancers of the learning processes and memory.

12 Claims, No Drawings

PYROGLUTAMIC ACID DERIVATIVES AS ENHANCERS OF LEARNING PROCESSES AND MEMORY AND PHARMACEUTICAL COMPOSITIONS COMPRISING SAME

SUMMARY OF THE INVENTION

The present invention relates to pyroglutamic acid derivatives of general formula (I)

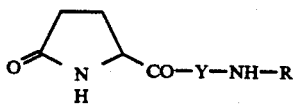
(I)

wherein R is selected from:
2-(N,N-diisopropyl)aminoethyl,
2-aminoethyl,
2-N-(pyrrolidin-2-one-1-yl)acetyl aminoethyl,
2-phenylethyl,
benzyl,
2-N-(pyroglutamylglycyl)aminoethyl,
2-N-(pyroglutamyl)aminoethyl;
Y is either a C—N single bond or the bivalent residue of an aminoacid selected from:

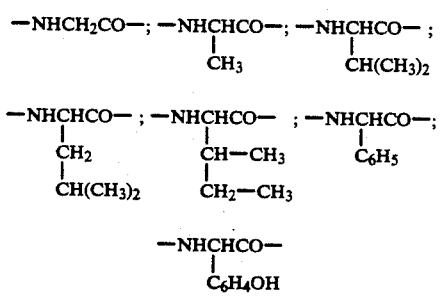

The compounds of formula (I) are nootropic substances, potent enhancers of learning processes and memory.

The present invention also relates to orally or parenterally administrable pharmaceutical compositions for enhancing the learning processes and memory, comprising a compound of formula (I) as active ingredient.

DESCRIPTION OF THE PRIOR ART

Pyroglutamic acid, that can be regarded as the parent compound of this class of compounds, is known to exhibit nootropic activity, however at doses 5 to 10 times as high as that of oxiracetam (Pharma. Res. Comm. 19, 901–912, 1987).

Some compounds which, having regard to their structure and pharmacological activity, are close to the compounds of general formula (I) are disclosed in Khim. Parm. Zh. 19/11, 1322-9, 1985 and in GB 2.185.483.

However, the known compounds exhibit a lower activity than that of the compounds of the present invention. Among the marketed compounds, those which are more closely related to the compounds of general formula (I) are Piracetam (Curr. Rev. Psycopharm 3, 22, 1976) and Oxiracetam (Il Farmaco, ed. Sci. 39/1, 16, 1984).

As hereinbelow described, the compounds of the present invention were shown to be more potent than the known compounds.

DETAILED DESCRIPTION OF THE INVENTION

Because of the presence of at least one chiral carbon atom (the carbon atom bound to —$NR_1R_2$), the compound of formula (I) can exist as two enantiomers designated (R) and (S); since the R and Y groups can contribute a further chiral center, the compounds of formula (I) can also exist as diastereomers; in both cases, the compounds of formula (I) can also exist as racemic mixtures. Since according to the foregoing references it has been found that both the optically active forms and the racemic mixtures are pharmacologically active, hereinbelow, for the sake of simplicity, no specific reference to the optical activity of the compounds shall be made.

The compounds of general formula (I) are prepared via the processes illustrated in the following reaction schemes.

In order to prepare the compounds wherein Y is a C—N single bond, the reaction scheme is as follows:

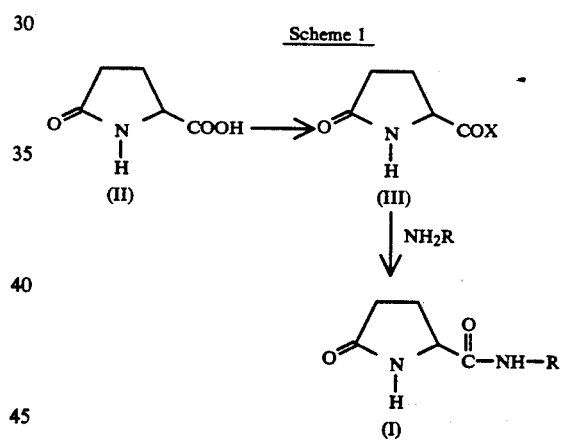

Pyroglutamic acid (II) is converted into the activated compound (III) (X=activating group) via a halogenating agent, such as e.g. thionyl chloride or oxalyl chloride, or via a condensating agent, such as e.g. dicyclohexylcarbodiimide (DCC), carbonyldiimidazole (CDI), 2-ethoxy-1-ethoxycarbonyl-1,2-dihydroquinoline (EEDQ) or is activated converting it into a short-chain alkyl ester. The activated compound (III) is then reacted with a stechiometric or excess amount of amine (IV) in a solvent-free environment or dissolved in an inert solvent, such as acetonitrile or methylene chloride, or (when EEDQ is used as activating agent) in acetonitrile-water.

The raw reaction product is purified by silica gel chromatography using ethyl acetate-methanol or chloroform-methanol as eluant. For the compounds wherein Y is an aminoacid residue, the reaction scheme is as follows:

Scheme 2

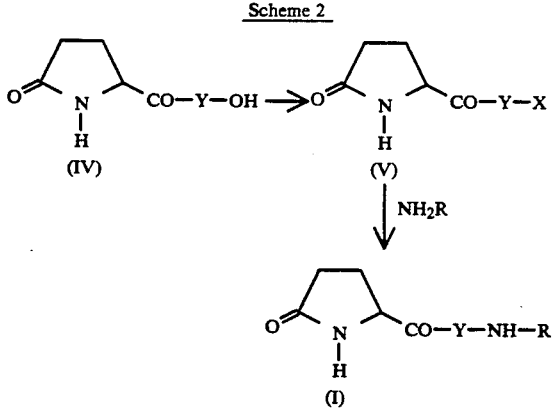

The reaction is carried out under the same operating conditions described in Scheme 1. For the compound ST 714 the reaction scheme is the following:

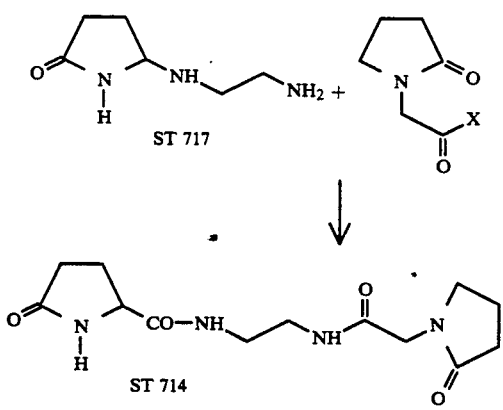

DESCRIPTION OF THE PREFERRED EMBODIMENTS

EXAMPLE 1

Preparation of N-(pyroglutamyl)-N',N''-(diisopropyl)ethylenediamine (ST 649)

N,N-diisopropylethylenediamine (1 g; 6.98 mmoles) was added to methyl pyroglutamate (1 g; 6.98 mmoles) in methanol (10 mL). The resulting solution was left under stirring at room temperature for 24 hours. Diisopropyl ether was then added till complete precipitation. 1.25 g of product were obtained by filtration.

Yield: 70%

M.P.=128°-129° C.

TLC=silica gel Eluant=CHCl$_3$—MeOH 7:3 RF=0.15

Elementary analysis for $C_{13}H_{25}N_3O_2$ Calculated C 61.14; H 9.86; N 16.45; Found C 61.45; H 10.01; N 16.12.

$^1$H NMR(CDCl$_3$): δ7.7 (br, 1H, —NHCHCO—), 7.1 (br t, 1H, NHCO—), 4.2 (m, 1H, C$\underline{H}$CO—), 3.4–1.9 (m, 10H, —NHC$\underline{H_2}$C$\underline{H_2}$N—, 2-C$\underline{H}$Me$_2$,—COC$\underline{H_2}$C$\underline{H_2}$-CH—), 1.05 (d, 12$\overline{H}$, 2—CHM$\underline{e_2}$)

HPLC

μ Bondapack-NH$_2$; Length=300 mm; Diameter=3.9 mm; size=10 μm

Eluant=KH$_2$PO$_4$ 0.05M-CH$_3$CN (35:65)

Flow rate=1 ml/min

Permanence time=6.09 min

EXAMPLE 2

Preparation of N-(pyroglutamyl)-ethylenediamine (ST 717)

Ethylenediamine (1.89 g; 31.5 mmoles) was added to methyl pyroglutamate (3 g; 21 mmoles) in methanol (50 mL) and the resulting solution was kept under stirring at room temperature for 24 hours. To this solution diethyl ethere was added under stirring till complete precipitation. 2.3 g of product were obtained by filtration.

Yield: 64%

M.P.=163°-165° C.

TLC=silica gel Eluant=MeOH RF=0.13

Elementary analysis for $C_7H_{13}N_3O_2$ Calculated C 49.11; H 7.65; N 24.54; Found C 49.14; H 7.81; N 24.77.

$^1$H NMR (D$_2$O): δ4.3 (m, 1H, —C$\underline{H}$CO—), 3.3 (t, 2H, —CONHC$\underline{H_2}$—), 2.75 (t, 2H, —C$\underline{H_2}$NH$_2$), 2.5–1.9 (m, 4H, —COC$\underline{H_2}$C$\underline{H_2}$CH—)

HPLC

Techsil-5NH$_2$; Length=300 mm; Diameter=3.9 mm; size=5 μm

Eluant=KH$_2$PO$_4$ 0.05M-CH$_3$CN (55:45)

Flow rate=1 ml/min

Permanence time=3.28 min

EXAMPLE 3

Preparation of N-(pyroglutamyl)-N'-[(pyrrolidin-2-one-1-yl)acetyl]ethylenediamine (ST 714)

EEDQ (2.16 g; 8.76 mmoles) and ST 717 (1 g; 5.84 mmoles) were added to (pyrrolidin-2-one-1-yl)acetic acid (836 mg; 5.84 mmoles) in CH$_3$CN (50 mL). Water was added till complete solubilization and the solution was kept under stirring at room temperature for 24 hours. The solvents were evaporated under vacuum, the residue was taken up with methanol and Et$_2$O was added under stirring. The precipitate was filtered off and chromatographed on silica gel using EtOAc-MeOH 1:1 as eluant, 1 g of product was obtained.

Yield: 58%

M.P.=161°-162° C.

TLC=silica gel Eluant=EtOAc-MeOH 1:1 RF=0.24

Elementary analysis for $C_{13}H_{20}N_4O_4$ Calculated C 52.69; H 6.80; N 18.90; Found C 52.48; H 7.08; N 19.08.

$^1$H NMR (D$_2$O): δ4.3 (m, 1H, —C$\underline{H}$CO—), 3.9 (s, 2H, COC$\underline{H_2}$NCO—), 3.6–3.3 (m, 6$\overline{H}$, —NC$\underline{H_2}$CH$_2$CH$_2$CO—, —NC$\underline{H_2}$C$\underline{H_2}$N—), 2.7–1.9 (m, 8H, —COC$\underline{H_2}$C$\underline{H_2}$C$\overline{H}$—, —COC$\underline{H_2}$C$\underline{H_2}$CH$_2$N—)

HPLC

Techsil-5NH$_2$; Length=300 mm; Diameter=3.9 mm; size=5 μm

Eluant=CH$_3$CN-KH$_2$PO$_4$ 0.05M (65:35)

Flow rate=1 ml/min

Permanence time=3.70 min

EXAMPLE 4

Preparation of N-(pyroglutamylglycyl)-benzylamine (ST 764)

CDI (27.63 g; 170.4 mmoles) and glycine ethyl ester hydrochloride (21.62 g; 154.9 mmoles) were added to D,L-pyroglutamic acid (20 g; 154.9 mmoles) in CH$_3$CN (800 mL). The mixture was kept at reflux temperature for 20 hours, the solvent was evaporated to ⅓ of the initial volume and the residue kept at 0° C. The solid thus formed was filtered off and recrystallized from CH$_3$CN giving 18.5 g of pyroglutamylglycine ethyl ester.

Yield: 56%

TLC=silica gel Eluant=EtOAc-MeOH 8:2 RF=0.43

$^1$H NMR (D$_2$O): δ4.4 (m, 1H, —CHCO—), 4.2 (q, 2H,CH$_2$CH$_3$), 4 (s, 2H, —CH$_2$CO—), 2.65-2.05 (m, 4H, —COCH$_2$CH$_2$CH—), 1.25 (t, 2H, —CHCH$_3$)

Benzylamine (15 g; 140 mmoles) was added to pyroglutamylglycine ethyl ester (3 g; 14 mmoles) and the resulting mixture was kept under stirring at room temperature for two days. ET$_2$O was added and the mixture was kept under stirring for one hour. The precipitated solid was filtered off and chromatographed on silica gel using EtOAc-MeOH 7:3 as eluant giving 3.4 g of product.

Yield: 88%
M.P.=174°-175° C.
TLC=silica gel Eluant=EtOAc-MeOH 7:3 RF=0.5
Elementary analysis for C$_{14}$H$_{17}$N$_3$O$_3$ Calculated C 61.08; H 6.22; N 15.26; Found C 61.26; H 6.47; N 15.42.

$^1$H NMR (DMSO-d$_6$): δ8.5 (br, 2H, —CONHCH$_2$CONH—), 8.0 (br, 1H, —CONHCH—), 7.38 (m, 5H, aromatics), 4.4 (m, 2H, —CH$_2$Ph), 4.2 (m, 1H, —CHCON—), 3.85 (m, 2H, —NCH$_2$CON—), 2.4-1.9 (m, 4H, —COCH$_2$CH$_2$CH—)

HPLC
μ Bondapack C$_{18}$; Length=300 mm; Diameter=3.9 mm; size=10 μm
Eluant=KH$_2$PO$_4$ 0.05M-CH$_3$CN (80:20)
Flow rate=1 ml/min
Permanence time=4.2 min

EXAMPLE 5

Preparation of N-(pyroglutamylglycyl)-phenethylamine (ST 760)

This compound was prepared as described in Example 4 starting from phenethylamine.

Yield: 86%
M.P.=146°-147° C.
TLC=silica gel Eluant=EtOAc-MeOH 7:3 RF=0.46
Elementary analysis for C$_{15}$H$_{19}$N$_3$O$_3$ Calculated C 62.27; H 6.62; N 14.52; Found C 62.13; H 6.67; N 14.69.

$^1$H NMR (DMSO-d$_6$): δ8.4 (br, 1H, —CONH—), 8.1 (br, 1H, —CONH—), 7.95 (br, 1H, —CONHCH—), 7.30 (m, 5H, aromatics), 4.15 (m, 1H, —CHCON—), 3.75 (m, 2H, —CONHCH$_2$CO—), 3.35 (m, 2H, —CONCH$_2$CH$_2$Ph), 2.78 (m, 2H, —CH$_2$Ph), 2.4-1.9 (m, 4H, —COCH$_2$CH$_2$CH—)

HPLC
μ Bondapack C$_{18}$; Length=300 mm; Diameter=3.9 mm; size=10 μm
Eluant=KH$_2$PO$_4$ 0.05M-CH$_3$CN (80:20)
Flow rate=1 ml/min
Permanence time=7.80 min

EXAMPLE 6

Preparation of N-(pyroglutamylglycyl)-ethylenediamine (ST 702)

Ethylenediamine (1.68 g; 28 mmoles) was added to pyroglutamylglycine ethyl ester (4 g; 18.7 mmoles) in CH$_3$CN (100 mL) and the resulting mixture was kept at the reflux temperature for 20 hours. After cooling to room temperature Et$_2$O was added under stirring. The solid thus formed was filtered off and chromatographed on silica gel using CHCl$_3$-MeOH 1:1 as eluant giving 1.5 g of product.

Yield: 35%
M.P.=192°-193° C.
TLC=silica gel Eluant=MeOH-CHCl$_3$ 6:4 RF=0.1

Elementary analysis for C$_9$H$_{16}$N$_4$C$_3$ Calculated C 47.36; H 7.06; N 24.54; Found C 46.91; H 7.28; N 24.12.

$^1$H NMR (D$_2$O): δ4.3 (m, 1H, —NCHCO—), 3.9 (s, 2H, —NCH$_2$CN—), 3.25 (t, 2H, —NCH$_2$CH$_2$NH$_2$), 3.7 (t, 2H, —NCH$_2$CH$_2$NH$_2$—), 2.5-1.9 (m, 4H, —COCH$_2$CH$_2$CH—)

HPLC
μ Bondapack-NH$_2$; Length=300 mm; Diameter=3.9 mm; size=10 μm
Eluant=CH$_3$CN-KH$_2$PO$_4$ 0.05M (65:35)
Flow rate=1 ml/min
Permanence time=7.28 min

EXAMPLE 7

Preparation of N-(pyroglutamylglycyl)-N',N'-(diisopropyl)-ethylenediamine (ST 685)

N,N-diisopropylethylenediamine (3.03 g, 21 mmoles) was added to pyroglutamylglycine ethyl ester (1.5 g; 7 mmoles) in CH$_3$CN (30 mL) and the resulting mixture was kept at the reflux temperature for 24 hours. The mixture was filtered and the filtrate added dropwise under stirring into an Erlenmayer flask containing Et$_2$O. 1.5 g of product were obtained by filtration.

Yield: 69%
M.P.=138°-139° C.
TLC=Silica gel Eluant=CHCl$_3$-MeOH-H$_2$O-NH$_4$OH 55:35:5:5 RF=0.6
Elementary analysis for C$_{15}$H$_{28}$N$_4$O$_3$ Calculated C 57.67; H 9.03; N 17.93; Found C 57.23; H 9.41; N 17.70.

$^1$H NMR (CDCl$_3$): δ8.0-7.6 (br, 2H, —CNH—, —CONHCH—), 6.9 (br, 1H, —CONH—), 4.25 (m, 1H, —CHCO—), 3.9 (d, 2H, —NHCH$_2$CO—), 3.4-1.9 (m, 10H, —NHCH$_2$CH$_2$N—, 2-CHMe$_2$, —COCH$_2$CH—), 1.05 (d, 12H, 2-CHMe$_2$)

HPLC
μ Bondapack NH$_2$; Length=300 mm; Diameter=3.9 mm; size=10 μm
Eluant=KH$_2$PO$_4$ 0.05M-CH$_3$CN (35:65)
Flow rate=1 ml/min
Permanence time=5.52 min

EXAMPLE 8

Preparation of N,N'-bis(pyroglutamylglycyl)ethylenediamine (ST 907)

Ethylenediamine (0.56 g; 9.35 mmoles) was added to pyroglutamylglycine ethyl ester (4 g; 18.7 mmoles) in MeOII (200 mL) and the resulting solution was kept under stirring at room temperature for 60 hours. The solvent was evaporated and the residue was chromatographed on silica gel using MeOH as eluant. 2.6 g of product were obtained.

Yield: 70%
M.P.=226°-229° C. (dec.)
TLC=Silica gel Eluant=MeOH RF=0.53
Elementary analisy for C$_{16}$H$_{24}$N$_6$O$_6$ Calculated C 48.48; H 6.10; N 21.20; Found C 48.10; H 6.22; N 20.90.

$^1$H NMR (D$_2$O): δ4.4 (m, 2H, 2-NCHCO—), 3.92 (s, 4H, 2-NCH$_2$CON—), 3.35 (s, 4H, —NCH$_2$CH$_2$N—), 2.68-2.05 (m, 8H, 2—COCH$_2$CH$_2$CH—)

HPLC
μ Bondapack-NH$_2$; Length=300 mm; Diameter=3.9 mm; size=10 μm
Eluant=CH$_3$CN-KH$_2$PO$_4$0.05 M(65:35)
Flow rate=1 ml/min
Permanence time=5.49 min

EXAMPLE 9

Preparation of N,N'-bis(pyroglutamyl)ethylenediamine (ST 908)

Ethylenediamine (0.631 g; 10.5 mmoles) was added to methyl pyroglutamate (3 g; 21 mmoles) in MeOH (50 mL) and the resulting solution was kept under stirring at room temperature for 24 hours. The solvent was evaporated and the residue chromatographed on silica gel using MeOH as eluant. 2.13 g of product were obtained.

Yield: 72%

M.P.=222°-225° C. (dec.)

TLC=Silica gel Eluant=MeOH RF=0.52 elementary analysis for $C_{12}H_{18}N_4O_4$ Calculated C 51.05; H 6.43; N 19.84; Found C 51.48; H 6.37; N 19.35;

$^1$H NMR ($D_2O$): δ4.3 (m, 2H, 2-N$\underline{CH}$CO—), 3.4 (s, 4H, —N$\underline{CH_2CH_2}$N—), 2.6–2.0 (m, 8$\overline{H}$, 2-CO$\underline{CH_2CH_2}$-CH—)

HPLC

μ Bondapack-$NH_2$; Length=300 mm; Diameter=3.9 mm; size=10 μm

Eluant=$CH_3CN$-$KH_2PO_4$ 0.05M (65:35)

Flow rate=1 ml/min

Permanence time=4.60 min (A) Assessment of the antiamnesic activity

In order to assess the antiamnesic activity the passive avoidance test in mice was used. Amnesia was brought about by administration of scopolamine (cfr. Bammer, Pharmacological investigations of neurotransmitter involvement in passive avoidance responding: a review and some new results. *Neurosci. Biobehav. Rev.*, 6 (3) 247–296, 1982); or by electroconvulsive shock (ECS) (cfr. Banfi et al., A screening method for substances potentially active on learning and memory. *J. Pharmacol. Methods* Vol.: 8 (4) 255–263, 1982).

Male CD1 mice (Charles River, Italy) weighing 25–26 g were used for the scopolamine-induced amnesia test.

Male CD1 mice (Charles River, Germany) fed on a normal diet, were used for the ECS-induced amnesia test.

The compounds were administered i.p. at doses equimolar to 1 mg/kg oxiracetam in the scopolamine-induced amnesia test; and 10 and 1 mg/kg oxiracetam in the ECS-induced amnesia test.

The compounds were dissolved in saline.

The apparatus for passive avoidance conditioning was a black plastic chamber (42×42 cm, height 40 cm) provided with a floor constructed of metal rods that could be electrified. From the front wall extended a white runway, 30 cm long and 10 cm wide provided with side walls 12 cm high, which led into the box through a guillotine door. The runway was lightened by a 60 W lamp whereas the box remained in the dark (cfr. Ader et al., Retention of passive avoidance response as a function of the intensity and duration of electric shock. *Psychon. Sci.*, 26 (3), 125–127, 1972).

Passive avoidance following scopolamine-induced amnesia

The animals were administered the compounds and scopolamine (1.5 mg/kg s.c.) 30 minutes and 15 minutes, respectively, before the test and were then placed on the runway. After one minute of adaptation, the door was raised and the time employed by the animal to enter the darkened box with all four feet, was recorded.

Upon entry, the guillotine door was lowered and three seconds thereafter the rods were electrified, 0.21 mA for 2 seconds.

Immediately thereafter the animal was placed in the housing cage. Retention was assessed 24 hours later by placing the animal on the runway and again evaluating the latency in entering the chamber, using an endpoint of 300 s (cfr. Bammer, loc. cit.).

Passive avoidance following ECS-induced amnesia 30 minutes following treatment with the compounds, the animals were placed on the runway. After one minute of adaptation, the door was raised and the time employed by the animal to enter the darkened box with all four feet was recorded.

Upon entry, the guillotine door was lowered and three seconds thereafter the rods were electrified, 0.24 mA for 2 seconds.

The mouse was then removed from the chamber and immediately administered an electroshock delivered through spring clips attached to the ears (square wave, intensity 20 mA, amplitude 0.6 msec, duration 0.5 s, frequency 50 Hz).

Immediately thereafter the animal was placed in the housing cage. Retention was assessed 24 hours later by placing the animal on the runway and again evaluating the latency in entering the chamber, using an endpoint of 300 seconds (Bammer, loc. cit.).

In each experiment, two groups of animals in addition to the treated ones were used, that were defined as follows:

(1) ceiling control animals (treated with placebo and not subjected to amnesia treatment with scopolamine or ECS) to ensure that these animals not treated with the amnesia agent remembered the task;

(2) base-line control animals (treated with placebo and subjected to amnesia treatment with scopolamine or ECS) to ensure that ECS or scopolamine produced amnesia in the animals not treated with the compounds of the present invention.

The results of each compound under examination were expressed as percentage of amnesia reversal (AR) in order to make comparisons across the tested compounds.

$$AR \text{ is defined as follows: } AR = \frac{CI_t}{CI_c} \cdot 100$$

wherein CI, Comparison Index (the subscripts "t" and "c" refer to "treated" and "ceiling control", respectively) is defined by the formula $$CI=[\Sigma Aij/Ni.Nj)]100$$

wherein

Ni is the number of animals belonging to the i-nth group (ceiling control or treated animals);

Nj is the number of animals belonging to the j-nth group (base-line control animals); and Aij is a binary function that can take only the values −1,0 or −1 depending on whether the latency time (in seconds) of an animal belonging to the i-nth group, Xi, is higher than, the same as or smaller than the latency time (in seconds) of an animal of the j-nth group, Xj.

The sum ΣAij encompasses all the possible pairs obtained by combining each term Xi with each term Xj.

Whenever in performing the test the Comparison Index (CI) between ceiling control animals and baseline control animals, generally expected to range between 60 and 80%, turned out to be lower than 40% the data for the whole experiment were discarded.

The results are shown in Table 1

TABLE 1

Passive avoidance following scopolamine-induced and ECS induced amnesia
The table shows the ARs of some compounds of the present invention. The number of animals (No.) and the AR of each compound tested at various dose levels are reported.

|  | ECS | | | | SCOPOLAMINE | |
|---|---|---|---|---|---|---|
|  | 10 mg/kg | | 1 mg/kg | | 1 mg/kg | |
|  | No. | % AR | No. | % AR | No. | % AR |
| Ceiling control group | 82 | 100 | 82 | 100 | 371 | 100 |
| Base-line control group | 153 | 0 | 153 | 0 | 649 | 0 |
| Piracetam | 30 | 0 | 27 | 0 | 34 | 25 |
| Oxiracetam | 32 | 8 | 31 | 31 | 23 | 0 |
| ST 702 | 24 | 69 | 12 | 50 | 23 | 16 |
| ST 714 | 12 | 53 | 12 | 0 | 12 | 0 |
| ST 907 | 36 | 57 | 35 | 25 | 12 | 17 |
| ST 908 | 12 | 17 | 12 | 46 | 23 | 46 |

(B) Behavioural profile

The behavioural profile was assessed in male CDI mice (Charles River, Italy) weighing 22–24 g, using the Irwin test (IRWIN S., Drug screening and evaluation procedures; 136, 123–128 1962). The animals had been caged under normal conditions and kept fasting for the last 18 hours. Following administration of the compounds, the behaviour of the animals was monitored for 6 hours.

The compounds were suspended in 10% arabic gum and orally administered at doses equimolar to 90, 23, 5.4 and 1.4 mg piracetam/10 mL/kg of body weight.

The animals of the control groups were administered 10% arabic gum (10 mL/kg, orally).

No compound altered, at the tested doses, the behavioural profile.

(C) Analgesic activity

The analgesic activity was assessed in CDI mice (Charles River, Italy) weighing 22–24 g, utilizing the hot plate test (56° C.).

The animals, kept under normal caging conditions and kept fasting for 18 hours, were placed on the hot plate for 30, 60, 120 and 180 minutes following the oral administration of 90, 23, 5.4 and 1.4 mg/10 mL/kg equimolar to piracetam of each compound under examination.

The analgesic activity was assessed by measuring the increase (in seconds) of the time the animals continued to stay on the hot plate. None of the tested compounds was shown to possess analgesic activity.

Pharmaceutical compositions in unit dosage form comprise between about 100 and about 500 mg of active ingredient.

What is claimed is:

1. Pyroglutamic acid derivative of formula (I)

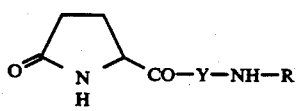

(I)

wherein R is selected from:
 2-(N,N-diisopropyl)aminoethyl,
 2-aminoethyl,
 2-N-(pyrrolidin-2-one-1-yl)acetyl aminoethyl,
 2-phenylethyl, only when Y is a bivalent radical of an amino acid selected from the group below,
 benzyl, only when Y is a bivalent radical of an amino acid selected from the group below,
 2-N-(pyroglutamylglycyl)aminoethyl,
 2-N-(pyroglutamyl)aminoethyl;

Y is either a C—N single bond or the bivalent radical of an aminoacid selected from:

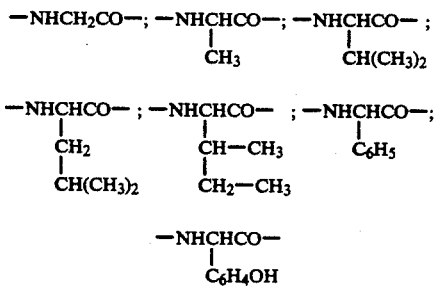

2. The compound of claim 1 wherein Y is a C—N single bond and R is 2-(N,N-diisopropyl)aminoethyl.

3. The compound of claim 1 wherein Y is a C—N single bond and R is aminoethyl.

4. The compound of claim 1 wherein Y is a C—N single bond and R is 2-N-(pyrrolidin-2-one-1-yl)acetyl aminoethyl.

5. The compound of claim 1 wherein Y is —NHCH$_2$CO— and R is benzyl.

6. The compound of claim 1 wherein Y is —NHCH$_2$CO— and R is 2-phenylethyl.

7. The compound of claim 1 wherein Y is —NHCH$_2$CO— and R is 2-aminoethyl.

8. The compound of claim 1 wherein Y is —NHCH$_2$CO— and R is 2-(N,N-diisopropyl)aminoethyl.

9. The compound of claim 1 wherein Y is —NHCH$_2$CO— and R is 2-N-(pyroglutamylglycyl)aminoethyl.

10. The compound of claim 1 wherein Y is —NHCH$_2$CO— and R is 2-N-(pyroglutamyl)aminoethyl.

11. An orally or parenterally administrable pharmaceutical composition for enhancing learning processes and memory, comprising as active ingredient a pyroglutamic acid derivatives of the formula (I)

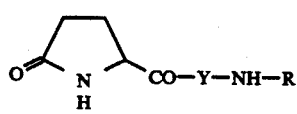

(I)

wherein R is selected from:
 2-(N,N-diisopropyl)aminoethyl,
 2-aminoethyl,
 2-N-(pyrrolidin-2-one-1-yl)acetyl aminoethyl,
 2-phenylethyl, only when Y is a bivalent residue of an amino acid selected from the group below,
 benzyl, only when Y is a bivalent radical of an amino acid selected from the group below,
 2-N-(pyroglutamylglycyl)aminoethyl,
 2-N-(pyroglutamyl)aminoethyl;

Y is either a C—N single bond or the bivalent radical of an aminoacid selected from:

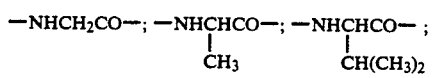
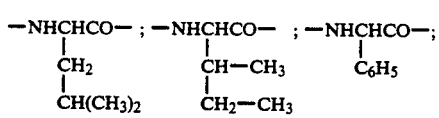
and a pharmacologically acceptable excipient.
12. The pharmaceutical composition of claim 11, in unit dosage form, comprising between about 100 to about 500 mg of a compound of formula (I).
* * * * *